US010925924B2

(12) United States Patent
Fischer

(10) Patent No.: US 10,925,924 B2
(45) Date of Patent: Feb. 23, 2021

(54) DRY-POWDER PEPTIDE MEDICAMENT

(71) Applicant: Apeptico Forschung UND Entwicklung GMBH, Vienna (AT)

(72) Inventor: Bernhard Fischer, Vienna (AT)

(73) Assignee: APEPTICO FORSCHUNG UND ENTWICKLUNG GMBH, Vienna (AT)

( * ) Notice: Subject to any disclaimer, the term of this patent is extended or adjusted under 35 U.S.C. 154(b) by 38 days.

(21) Appl. No.: 15/126,794

(22) PCT Filed: Mar. 17, 2015

(86) PCT No.: PCT/EP2015/055481
§ 371 (c)(1),
(2) Date: Sep. 16, 2016

(87) PCT Pub. No.: WO2015/140125
PCT Pub. Date: Sep. 24, 2015

(65) Prior Publication Data
US 2017/0087207 A1      Mar. 30, 2017

(30) Foreign Application Priority Data
Mar. 18, 2014   (EP) .................................... 14160540

(51) Int. Cl.
| A61K 9/00 | (2006.01) |
| A61K 9/14 | (2006.01) |
| A61K 38/00 | (2006.01) |
| A61K 38/12 | (2006.01) |
| A61K 31/351 | (2006.01) |
| A61K 31/215 | (2006.01) |
| A61K 31/7012 | (2006.01) |
| A61K 45/06 | (2006.01) |

(52) U.S. Cl.
CPC ............ *A61K 38/12* (2013.01); *A61K 9/0075* (2013.01); *A61K 9/145* (2013.01); *A61K 31/215* (2013.01); *A61K 31/7012* (2013.01); *A61K 45/06* (2013.01)

(58) Field of Classification Search
None
See application file for complete search history.

(56) References Cited

U.S. PATENT DOCUMENTS 6,315,983 B1 * 11/2001 Eistetter ............... A61K 9/0082
424/45
8,236,750 B2 * 8/2012 Schaefer ............... A61K 38/191
424/85.1

FOREIGN PATENT DOCUMENTS

| CN | 101453988 A | 6/2009 |
| CN | 103200955 A | 7/2013 |
| WO | WO-03047618 A2 * | 6/2003 | ............ A61K 39/35 |
| WO | 2010099556 A1 | 9/2010 |
| WO | WO 2011160664 A1 * | 12/2011 | ............ A61K 38/12 |
| WO | 2012065201 A1 | 5/2012 |
| WO | 2015140125 A2 | 9/2015 |
| WO | 2015140125 A3 | 9/2015 |

OTHER PUBLICATIONS

Innovagen, peptide solubility calculator, available on line at https://pepcalc.com/peptide-solubility-calculator.php, accessed on Jun. 18, 2019. (Year: 2019).*
Innovagen, peptide solubility calculator, available on line at https://pepcalc.com/peptide-solubility-calculator.php, accessed on Dec. 27, 2019. (Year: 2019).*
Innovagen, peptide solubility calculator, archived on Jan. 30, 2013, available online at https://web.archive.org/web/20130120053951/http://pepcalc.com (Year: 2013).*
Allison, D., et al., "Hydrogen Bonding between Sugar and Protein Is Responsible for Inhibition of Dehydration-Induced Protein Unfolding." Archives of Biochemistry and Biophysics, vol. 365 No. 2, May 15, 1999, pp. 289-298.
Baginski, L., et al., "In Vitro and in Vivo Characterisation of PEG-Lipid-Based Micellar Complexes of Salmon Calcitonin for Pulmonary Delivery." Pharmaceutical Research, Jun. 2012, vol. 29, pp. 1425-1434.
Brand, P., et al., "Peripheral Deposition of α1-protease Inhibitor using commercial Inhalation Devices." European Respiratory Journal, 2003, vol. 22, pp. 263-267.
Chang, L., et al., "Mechanisms of Protein Stabilization in the Solid State." Journal of Pharmaceutical Sciences, vol. 98, No. 9, Sep. 2009, pp. 2886-2908.
Edge, S., et al., "Factors Affecting Defining the Quality and Functionality of Excipients Used in the Manufacture of Dry Powder Inhaler Products." Drug Development and Industrial Pharmacy, 2008, vol. 34, pp. 966-973.
Elia, N., et al., "Functional Identification of the Alveolar Edema Reabsorption Activity of Murine Tumor Necrosis Factor-60 ." American Journal of Respiratory and Critical Care Medicine, vol. 168, No. 9, Nov. 1, 2003, pp. 1043-1050.
Geller, D., "Comparing Clinical Features of the Nebulizer, Metered-Dose Inhaler, and Dry Powder Inhaler." Respiratory Care, vol. 50. No. 10, Oct. 2005, pp. 1313-1322.

(Continued)

*Primary Examiner* — Julie Ha
*Assistant Examiner* — Kristina M Hellman
(74) *Attorney, Agent, or Firm* — Singleton Law, PLLC; Chainey P. Singleton

(57) ABSTRACT

Disclosed is a dry-powder peptide medicament with a non-typical concentration of carbohydrate excipient, as well as said medicament for use in treatment or prevention of a disease or condition, as well as methods for manufacturing said medicament.

20 Claims, 4 Drawing Sheets

Figure 1:
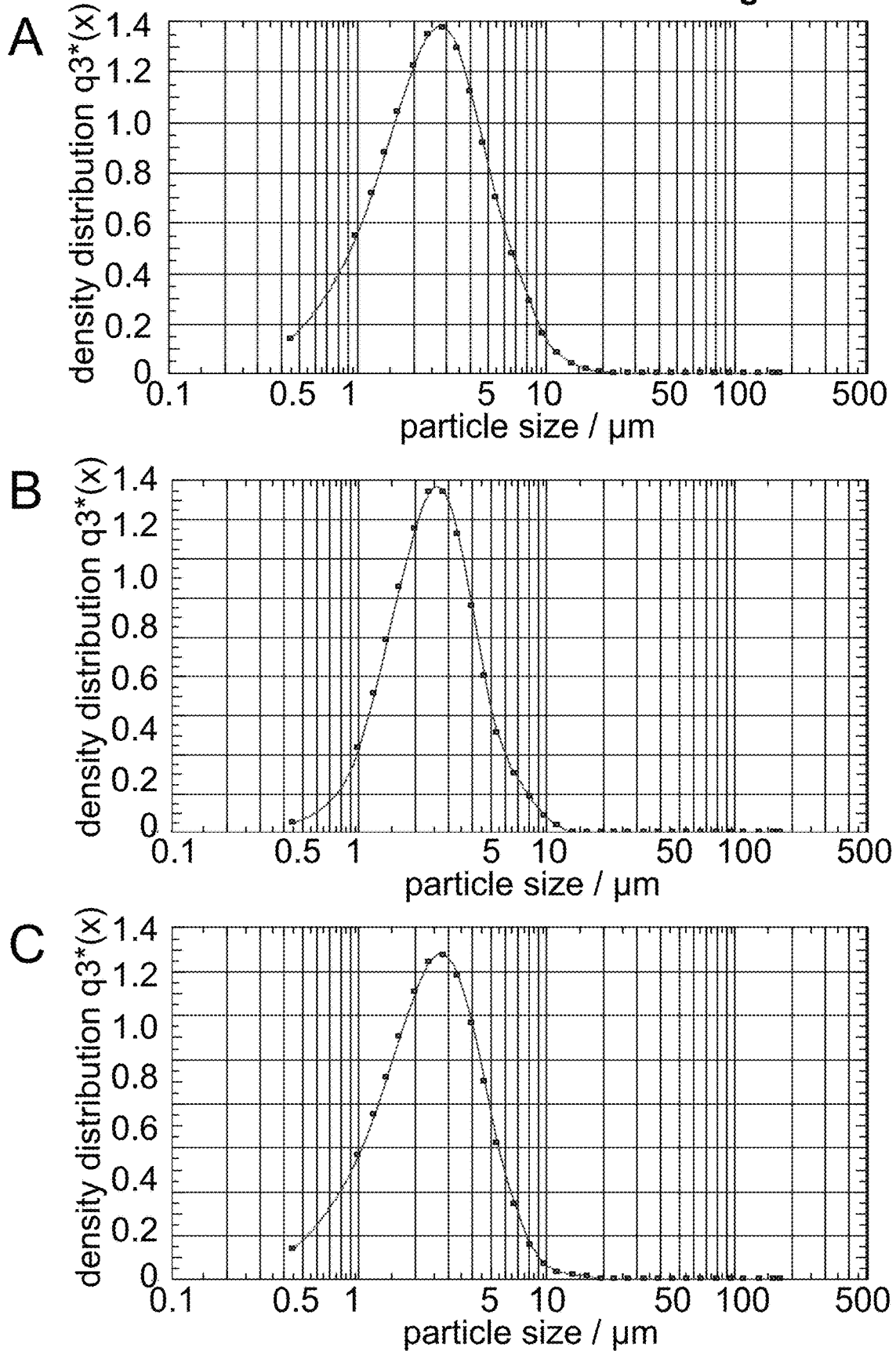

Specification includes a Sequence Listing.

(56) References Cited

OTHER PUBLICATIONS

Hribar, M., et al., "The lectin-like Domain of Tumor Necrosis Factor-α Increases Membrane Conductance in Microvascular Endothelial cells and Peritoneal Macrophages." European Journal of Immunology, Oct. 1999, vol. 29, No. 10, pp. 3105-3111.
International Preliminary Report on Patentability PCT/EP2015/055481 dated Apr. 25, 2016.
Jevsevar, S., et al., "PEGylation of therapeutic proteins." Biotechnology Journal, Jan. 2010, Vo. 5, No. 1, pp. 113-128.
Lee, K. et al., Intrapulmonary Potential of Polyethylene Glycol-modified Glucagon-like Peptide-1s as a type 2 Anti-Diabetic Agent. Regulatory Peptides, vol. 152, Jan. 2009, pp. 101-107.
Mack, G., "Pfizer dumps Exubera." Nature Biotechnology, Dec. 2007, vol. 25, No. 12, pp. 1331-1332.
Malcolmson, R., et al., "Dry Powder Formulations for Pulmonary Delivery." Pharmaceutical Science & Technology Today, vol. 1, No. 9, Dec. 1998, pp. 394-398.
Maltesen, M., et al., "Design of Experiments-Based Monitoring of Critical Quality Attributes for the Spray-Drying Process of Insulin by NIR Spectroscopy." AAPS PharmSciTech, vol. 13, No. 3, Sep. 2012, pp. 747-755.
Marquardt, A., et al., "Identification, Affinity Characterisation and Biological Interactions of Lectin-like peptide—Carbohydrate Complexes Derived from Human TNF-α using High-resolution Mass Spectrometry." Journal of Peptide Science, vol. 13, No. 12, Dec. 2007, pp. 803-810.
Morris, C., et al., "Pegylation of Antimicrobial Peptides Maintains the Active Peptide Conformation, Model Membrane Interactions, and Antimicrobial Activity while Improving Lung Tissue Biocompatibility following Airway Delivery." Antimicrobial Agents and Chemotherapy, vol. 56, No. 6, Jun. 2012, pp. 3298-3308.
Ogain, O., et al., "Particle Engineering of Materials for Oral Inhalation by dry Powder Inhalers. I—Particles of sugar Excipients (trehalose and raffinose) for Protein Delivery." International Journal of Pharmaceutics, vol. 405, Feb. 2011, pp. 23-35.
Owens, D. R., et al., "Alternative Routes of Insulin Delivery." Diabetic Medicine, vol. 20, No. 11, Nov. 2003, pp. 886-898.
Patton, J., et al., "Drug Delivery Strategies for Proteins & Peptides From Discovery & Development to Life Cycle Management." vol. 4 No. 8, Oct. 2004, http://www.drugdeliverytech.com.
Patton, J., et al., "Inhaling Medicines: Delivering Drugs to the Body through the Lungs." Nature Reviews Drug Discovery, vol. 6, Jan. 2007, pp. 67-74.
Pilcer, G., et al., "Formulation Strategy and use of Excipients in Pulmonary Drug Delivery." International Journal of Pharmaceutics, vol. 392, Jun. 2010, pp. 1-19.
Piroozia, N., et al., "Encapsulation of Alpha-1 Antitrypsin in PLGA Nanoparticles: In Vitro Characterization as an Effective Aerosol Formulation in Pulmonary Diseases." Journal of Nanobiotechnology, vol. 10, No. 20, 2012, pp. 1-15.
Pisal, D., et al. "Delivery of Therapeutic Proteins." Journal of Pharmaceutical Sciences, vol. 99, No. 6, Jun. 2010, pp. 2557-2575.
Roberts, M., J. et al., "Chemistry for peptide and protein PEGylation." Advanced Drug Delivery Reviews, vol. 54, Jan. 2002, pp. 459-476.
Schwameis R., et al., "A FIM Study to Assess Safety and Exposure of Inhaled Single Doses of AP30 1-A Specific ENaC Channel Activator for the Treatment of Acute Lung Injury." The Journal of Clinical Pharmacology, vol. 54, No. 3, Mar. 2013, pp. 341-350.
Shabbir, W., et al.,"Mechanism of Action of Novel Lung Edema Therapeutic AP301 by Activation of the Epithelial Sodium Channel." Molecular Pharmacology, vol. 84, Dec. 2013, pp. 899-910.
Sinsuebpol, et al., "Preparation and in Vivo Absorption Evaluation of Spray Dried Powders Containing Salmon Calcitonin Loaded Chitosan Nanoparticles for Pulmonary Delivery." Drug Design, Development and Therapy, vol. 7, Aug. 27, 2013, pp. 861-873.
Steckel, H., et al., "Alternative Sugars as Potential Carriers for Dry Powder Inhalations." International Journal of Pharmaceutics, vol. 270, Feb. 2004, pp. 297-306.
Tewes F., et al., "Development and Characterisation of Soluble Polymeric Particles for pulmonary Peptide Delivery." European Journal of Pharmaceutical Sciences, vol. 41, No. 2, Oct. 9, 2010, pp. 337-352.
Tiwari, G., et al., "Drug Delivery Systems: An Updated Review." International Journal of Pharmaceutical Investigation, vol. 2, No. 1, Jan. 2012, pp. 1-10.
Tzotzos, S., et al., "AP301, a Aynthetic Peptide Mimicking the Lectin-like Domain of TNF, Enhances Amiloride-sensitive Nab Current in Primary dog, pig and rat Alveolar type II Cells." Pulmonary Pharmacology & Therapeutics, vol. 26, No. 3, Jun. 2013, pp. 356-363.
Vander Goot, F., et al., "Membrane Interaction of TNF is not Sufficient to Trigger Increase in Membrane Conductance in Mammalian Cells." FEBS Letters, vol. 460, No. 1, Oct. 22, 1999, 107-111.
Veronese, F., et al., "PEGylation, Successful Approach to Drug Delivery." Drug Discovery Today, vol. 10, No. 21, Nov. 2005, pp. 1451-1458.
Zeng, X. etal., "The influence of carrier morphology on drug delivery by dry powder inhalers" International Journal of Pharmaceutics 200 (2000) 93-106.
Written Opinion and Search Report PCT/EP2015/055481 dated Jan. 11, 2015.
China Search Report dated Mar. 28, 2019, pp. 1-2.
Chinese Office Action dated Mar. 28, 2019, pp. 1-7.
Chinese Office Action dated Mar. 28, 2019 (English Translation), pp. 1-7.

\* cited by examiner

DRY-POWDER PEPTIDE MEDICAMENT

The present invention relates to an inhalation formulation of a peptide medicament.

TIP peptides are peptides comprising the human tumour necrosis factor (TNF) lectin-like domain (TIP domain). The TIP domain is covered for instance by van der Goot et al, 1999, PubMed unique identifier (PMID) 10571070. As used herein, TIP peptides consist of 7-17 amino acids including the hexamer $TX_1EX_2X_3E$ (SEQ ID NO: 6), wherein $X_1$, $X_2$ and $X_3$ can be any natural or non-natural amino acid, wherein the peptide does not exhibit TNF-specific inflammatory activity (Hribar et al, 1999, PMID 10540321; Elia et al, 2003, PMID 12842853) and may be cyclised. The biological activity of TIP peptides such as AP301 (cyclo-CGQRETPEGAEAKPWYC; CGQRETPEGAEAKPWYC is SEQ ID NO: 1) comprises activation of the amiloride-sensitive epithelial sodium channel (ENaC), as reported by Tzotzos et al, 2013, PMID 23313096.

TIP peptides are known for instance from European Patents EP 1 247 531 B1 and EP 1 264 599 B1 for use in the treatment of edema, especially pulmonary edema. Such peptides are also known for use in the treatment and prevention of vascular complications in diabetes patients such as micro- and macroangiopathy, myocardial infarction, microvascular cardiac hyperpermeability, stroke, neuropathy, retinopathy, nephropathy or diabetic foot disease (EP 2582385). Moreover, such peptides are known for prevention of edema due to reduction in hyperpermeability, caused by injury of endothelial and/or epithelial layers, preferably edema occurring during treatment of pneumonia, acute lung injury, ARDS, bacterial or viral lung disease, more preferably edema occurring during infection by *Listeria monocytogenes, Streptococcus pneumoniae*, SARS virus, RSV or Influenza virus (EP 2403519, also published as WO 2010/099556 A1). In addition, such peptides are known for use in the treatment and prevention of the pulmonary form of altitude sickness (WO 2014/001177). Finally, such peptides are known for use in treatment or prevention of influenza, when administered together with an inhibitor of viral neuraminidase, preferably zanamivir or oseltamivir (WO 2012/065201 A1).

A TIP peptide has been assigned an orphan drug designation for use in the treatment and prevention of the pulmonary form of altitude sickness, by the EMA (EMA/OD/144/12) as well as by the US-FDA (12-3829).

The object of the present invention is to provide a stable and effective inhalation formulation with a TIP peptide as active agent (i.e. a novel formulation of one or more TIP peptides) and a method for manufacturing said medicament. Said medicament shall be suitable and effective for use in treatment or prevention of a disease or condition, wherein the medicament is administered to the patient by inhalation.

Therefore, the present invention discloses a novel formulation of a dry-powder peptide medicament with a non-typical concentration of carbohydrate excipient, as well as said medicament for use in treatment or prevention of a disease or condition, as well as methods for manufacturing said medicament.

In the course of the present invention, various inhalation formulations, including dry-powder formulations, of TIP peptide were studied. Surprisingly, it was found that sugars or sugar alcohols, which are the most commonly used excipients in prior art, significantly inhibit the biological activity of a TIP peptide. This is not known in prior art. By abolishing the reliance on carbohydrate carriers, the present invention provides a solution to the problem posed, with increased pharmaceutical activity of the medicament compared to prior-art inhalation formulations—especially dry-powder formulations—of other medicaments that usually include a carbohydrate carrier.

In a particularly preferred embodiment of the invention, the dry-powder medicament comprises peptide AP301 (cyclo-CGQRETPEGAEAKPWYC) as single active agent and does not contain any excipient. A preferred method for manufacturing said embodiment comprises spray drying.

The dry-powder formulation according to the present invention can be used for any indication of the peptide according to the present invention for which administration by inhalation is possible. Preferably, the dry-powder formulation according to the present invention, especially if it includes peptide AP301, is for use in treatment or prevention of a disease or condition selected from the group of treatment of edema, vascular complications in diabetes patients, prevention of edema due to reduction in hyperpermeability, the pulmonary form of altitude sickness and, when administered together with an inhibitor of viral neuraminidase, influenza.

Non-invasive delivery strategies for peptide and protein therapeutics are viewed as an attractive alternative to parenteral injection, which suffers from poor patient compliance and requires trained personnel (Patton & Bossard, Drug Development and Delivery 2004, "Drug Delivery Strategies for Proteins & Peptides From Discovery & Development to Life Cycle Management"; Tewes et al, 2010, PMID 20621184; Tiwari et al, 2012, PMID 23071954).

AP301 is currently being developed as a treatment for lung edema (Shabbir et al, 2013, PMID 24077967). A phase 2 clinical trial is currently being performed in intensive care patients to investigate the clinical Effect of repetitive orally inhaled doses of AP301 on alveolar liquid clearance in acute lung injury (ClinicalTrials.gov Identifier: NCT01627613). In this trial, a liquid wherein AP301 is dissolved is aerosolised for administration of the drug to the patient. Aerosols can be produced by nebulisers. Established nebuliser products are for instance Aeroneb® and Pari®. Schwameis et al. published a clinical trial wherein a solution comprising the peptide AP301 was administered to healthy male subjects using a nebuliser (Schwameis et al., 2014, PMID: 24515273).

Dry-powder inhalers (DPIs) may offer advantages over nebulisers and other inhalation devices (Geller, 2005, PMID 16185367). DPIs are devices for inhalation of dry-powder formulations by the patient. Such devices are for instance disclosed in U.S. Pat. Nos. 4,995,385 and 4,069,819. Established DPI products are for instance SPINHALER®, ROTAHALER®, FLOWCAPS®, INHALATOR®, DISKHALER® and AEROLIZER®.

Another reason to formulate TIP peptides as a dry-powder medicament (instead of delivery as an aerosol) is that systemic inhalation therapy has yet to be optimised; most existing aerosol systems have been designed for delivery of small molecule drugs and do not protect labile macromolecules such as peptides and proteins. Many formulation processes are too stressful for a fragile peptide or protein active pharmaceutical ingredient (API, also called "active agent" herein), leading to a potential loss of its biological activity.

The most common approach towards stabilising protein drugs is to remove water from the formulation (Chang and Pikal, 2009, PMID 19569054). Specific excipients, such as disaccharides, are usually present to prevent protein unfolding due to dehydration stress (Allison et al, 1999, PMID 10328824). Attachment of polyethylene glycol (PEG)

groups to peptides and proteins (PEGylation) (Roberts et al, 2002, PMID 12052709) stabilises their secondary structure (Morris et al, 2012, PMID 22430978) and renders them more resistant to proteolytic digestion by lung enzymes (Lee et al, 2009, PMID 18951927; Baginski et al, 2012, PMID 22322897), as well as improving retention by increasing molecular mass (Veronese & Pasut, 2005, PMID 16243265; Patton & Byron, 2007, PMID 17195033).

However, quite contrary to such prior-art formulations, the peptide according to the present invention retained stability without such stabilisers, especially without carbohydrate stabilisers.

This is also contrary to the accepted view that it is challenging to formulate peptides as dry-powder medicaments. Only a few inhalable peptide formulations have already been marketed, such as Pulmozyme and Exubera, although the latter has since been withdrawn due to problems with patient use and complexity of the inhaler device (Patton & Bossard, Drug Development and Delivery 2004, "Drug Delivery Strategies for Proteins & Peptides From Discovery & Development to Life Cycle Management"; Mack, 2007, PMID 18066009; Tewes et al, 2010, PMID 20621184).

For pulmonary delivery the particle size, particle size distribution and moisture content are critical (Patton & Byron, 2007, PMID 17195033). For small peptides it seems important to achieve drug deposition deeply in the lungs for optimum absorption rather than in the upper airways (Patton & Byron, 2007, PMID 17195033). In order to have a systemic effect, inhaled therapeutic particles must reach the alveoli and their aerodynamic diameter must not exceed 5 micrometres for optimal deposition in the distal lung (Maltesen et al, 2013, PMID 22585372). In the case of aerosols, particles with an aerodynamic diameter of 1-2 micrometres can be deposited with 90% efficacy, the majority of the aerosol depositing in alveoli-rich regions (Patton & Byron, 2007, PMID 17195033).

This challenge could as well be solved by the present invention, by providing a robust and suitable dry-powder manufacturing process which can comprise spray drying.

Particles with the optimal aerodynamic particle size can be manufactured in several ways, including air-jet milling and spray drying (Malcolmson & Embleton, PSTT, 1998, doi: 10.1016/S1461-5347(98)00099-6). Spray drying is used in the pharmaceutical industry to produce particles for inhalation. Spray-dried insulin has been a development candidate of several pharmaceutical companies and was the first protein therapeutic for pulmonary delivery to receive marketing authorisation (Mack, 2007, PMID 18066009). Various commercial devices are available for delivering aerosolised solutions of protein and peptide therapeutics to the lungs (Brand et al, 2009, PMID 12952258).

To obtain particles with optimal aerodynamic and deposition properties it was, however, common practice in the prior art to add a carrier to achieve effective aerosolisation properties (Ogain et al, 2011, PMID 21129458). Examples of carriers used in spray drying are sugars or sugar alcohols such as lactose, mannitol and sucrose (Steckel & Bolzen, 2004, PMID 14726144), polysaccharides such as chitosan (Sinsuebpol et al, 2013, PMID 24039397) and various polymers such as polyethlene glycol (PEG) (Patton & Bossard, Drug Development and Delivery 2004, "Drug Delivery Strategies for Proteins & Peptides From Discovery & Development to Life Cycle Management"; Jevsevar et al, 2010, PMID 20069580; Pisal et al, 2010, PMID 20049941), polyvinylpyrrolidone (PVP) (Tewes et al, 2010, PMID 20621184), poly(lactic acid) (PLA) and poly(lactic-co-glycolic acid) (PLGA) (Pisal et al, 2010, PMID 20049941; Pirooznia et al, 2012, PMID 22607686). Nearly all drypowder inhaler products already on the market rely on lactose, a sugar, as carrier material (Pilcer & Amighi, 2010, PMID 20223286), wherein lactose is the only excipient (Edge et al, 2008, PMID 18800257). Unfortunately, it has been found in the course of the present invention that such carbohydrate carriers had detrimental effect on the activity of the peptide to be administered according to the present invention. Therefore, such standard formulation was not usable for a peptide according to the present invention.

In conclusion, it was held consensus view prior to the present invention that the stabilisation of protein and peptide drugs delivered as inhaled aerosols or dry powder particles is essential to the maintenance of biological stability (Tewes et al, 2010, PMID 20621184). In the vast majority of DPI products, this is achieved by means of the sugar lactose as carrier. In the case of Exubera, the only DPI peptide medicament which had ever been approved by the FDA, the dry-powder formulation consists of insulin (approximately 60%, w/w) and excipients, principally mannitol as a stabiliser (Owens et al, 2003, PMID 14632713). A typical activeagent-to-carrier ratio for dry-peptide medicaments may hence be a ratio of 3 to 2 (w/w).

Figure 2:
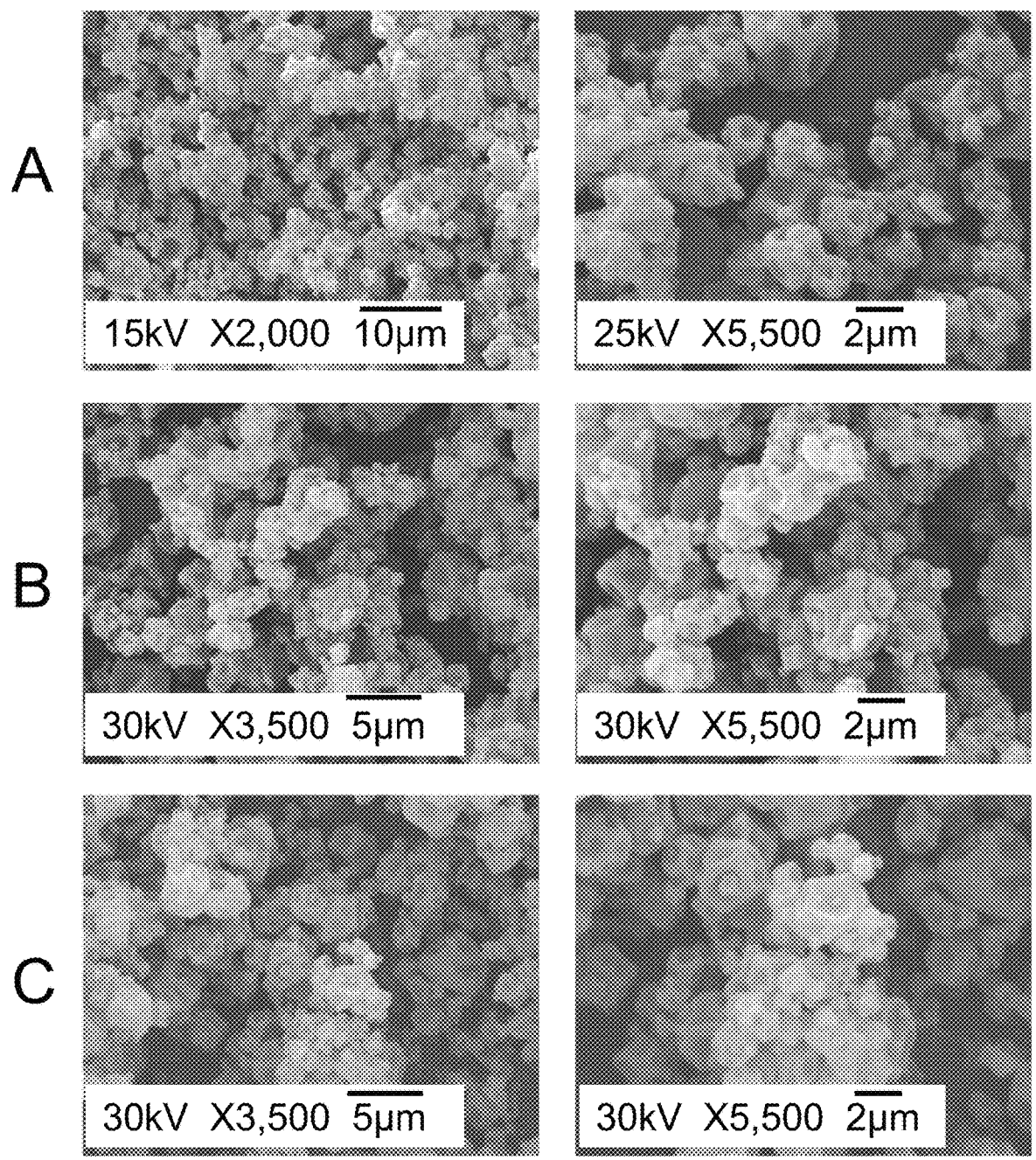

In spite of this consensus view, in the course of the present invention, it was found that a dry-powder peptide medicament can indeed be formulated without stabilisation by excipients (FIGS. 1 and 2). Surprisingly, besides the unexpected success in providing usable dry-powder formulations of a peptide according to the present invention without carbohydrate stabilisers, it even turned out that a dry-powder peptide medicament comprising said peptide, with a reduced amount of carbohydrate excipients, or with no excipients at all, offers the advantage of higher biological activity of the said peptide, compared to dry-powder formulations of said peptide stabilised according to the consensus view (cf. FIG. 3).

The dry-powder peptide medicament according to the present invention comprises a TIP peptide as active agent. Said peptide is a peptide according to the present invention. A peptide according to the present invention consists of 7-17 amino acids and includes the hexamer $TX_1EX_2X_3E$, wherein $X_1$, $X_2$ and $X_3$ can be any natural or non-natural amino acid, and wherein the peptide does not exhibit TNF-receptor-binding activity. Peptides according to the invention are known per se, e.g. from the following patent documents: EP 1 264 599 B1, US 2007/299003 A1, WO 94/18325 A1, WO 00/09149 A1, WO 2006/013183 A1 and WO 2008/148545 A1.

Figure 3:
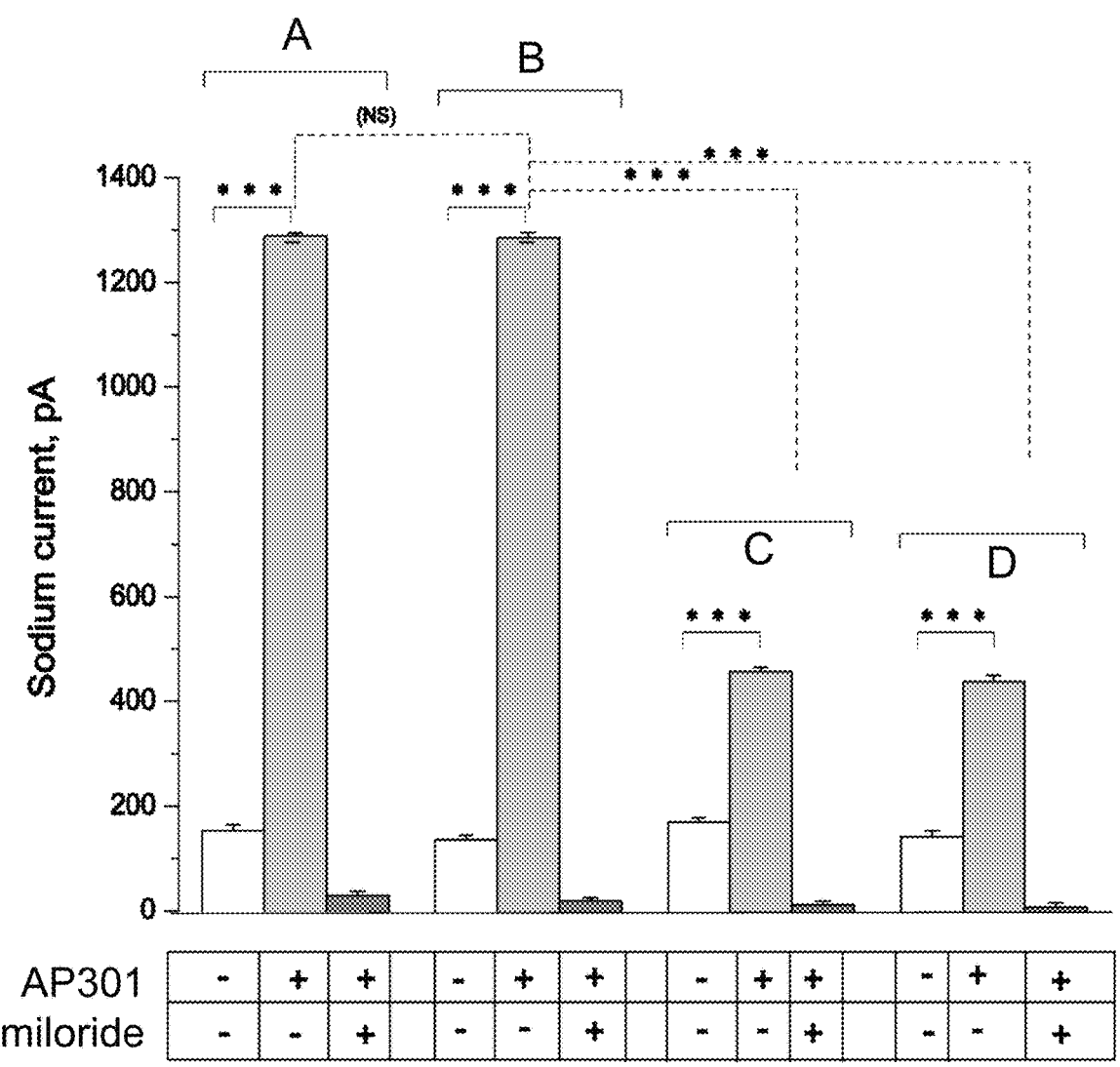

It is essential that the dry-powder medicament of the present invention has a carbohydrate concentration (w/w) less than 5%, preferably less than 1%, more preferably less than 0.1%, especially less than 0.01%. This is due to the surprising finding that carbohydrates inhibit the biological activity of a TIP peptide (FIG. 3). The inhibitory effect of carbohydrate in the dry-powder medicament becomes markedly detrimental (but tolerable in certain embodiments) at a carbohydrate concentration of 1% (w/w) or higher (provided it is less than 5%) and intolerably detrimental at a carbohydrate concentration of 5% (w/w) or higher (cf. Examples 2 and 3). It is, however, clear that low amounts or trace amounts of such inhibiting carbohydrates can be tolerated, if necessary.

In a preferred embodiment of the invention, the medicament comprises a peptide according to the present invention as single active agent. This may offer an advantage, as the addition of more active agents poses safety risks and may increase the cost of production.

In a particularly preferred embodiment of the present invention, the medicament does not contain any excipient. This may be advantageous over any other embodiment because any added excipient poses safety risks (due to potential impurities etc) and may increase the cost of production (due to regulatory requirements etc). FIGS. 1 and 2 show material properties of said preferred embodiment in comparison to dry-powder formulations of AP301 with sucrose or mannitol. They support the surprising finding that a formulation not containing any excipients is suitable for use in DPIs.

In another preferred embodiment of the present invention, the medicament does not contain any carbohydrate excipient. In another preferred embodiment of the present invention, the medicament does not contain any sugar excipient. In another preferred embodiment of the present invention, the medicament does not contain any sugar alcohol excipient. In another preferred embodiment of the present invention, the medicament does not contain any carbohydrate excipient selected from one or more of lactose, maltose, sucrose, trehalose, glucose, sorbitol, maltitol, mannitol and xylitol. In another preferred embodiment of the present invention, the medicament does not contain any mannitol excipient and does not contain any sucrose excipient.

In a preferred embodiment of the present invention, the peptide according to the present invention is cyclic (or circularised), in order to retain the original TNF-alpha conformation as much as possible (Elia et al, 2003, PMID 12842853), which may lead to higher biological activity. This is an optional feature, because, according to Marquard et al, 2007, PMID 17918767, peptide cyclisation may not be essential for carbohydrate binding important for biological activity.

In a preferred embodiment, in the medicament of the present invention the concentration (w/w) of any compound selected from the group of sugar(s) or sugar alcohol(s) such as lactose, maltose, sucrose, trehalose, glucose, sorbitol, maltitol, mannitol and xylitol is less than 5%, preferably less than 1%, more preferably less than 0.1%, especially less than 0.01%. There is experimental evidence that a sugar (alcohol) inhibits the biological activity of a peptide according to the invention (FIG. 3). Lactose, maltose, sucrose, trehalose, glucose, sorbitol, maltitol, mannitol and xylitol are all known as potential carriers in inhalation formulations (Pilcer & Amighi, 2010, PMID 20223286).

Preferably, the peptide according to the invention includes the amino-acid hexamer TPEGAE (SEQ ID NO: 2), which is the potential carbohydrate-binding motif (Marquardt et al, 2007, PMID 17918767) and may increase biological activity.

In a preferred embodiment, the peptide of the present invention includes the amino-acid hexamer TPEGAE (SEQ ID NO: 2). Preferably, the peptide is cyclic and contains a sequence of consecutive amino acids selected from the group comprising

QRETPEGAEAKPWY (SEQ ID NO: 3)

PKDTPEGAELKPWY (SEQ ID NO: 4)

CGQRETPEGAEAKPWYC (SEQ ID NO: 1)

CGPKDTPEGAELKPWYC (SEQ ID NO: 5)
and fragments of at least seven amino acids containing the hexamer TPEGAE (SEQ ID NO: 2). Such peptides or fragments thereof can have a biological activity as for instance shown in WO 2014/001177.

In a particularly preferred embodiment, the peptide according to the present invention is the peptide AP301 (CGQRETPEGAEAKPWYC), wherein AP301 is cyclised via the C residues, preferably by a disulfide bond between the C residues. Said peptide is already known from a phase 2 clinical trial (ClinicalTrials.gov Identifier: NCT01627613), which implies that by using said embodiment of the present invention one can build on already existing safety data, etc.

Preferably, the medicament of the present invention consists of powder particles of a mean diameter of 0.5 to 10 micrometres, preferably of a mean diameter of 1 to 5 micrometres, more preferably a mean diameter of 1 to 3.5 micrometres. This is to achieve efficient deposition in the lungs, as also explained above.

In a preferred embodiment, the medicament of the present invention is for use in treatment or prevention of a disease or condition, wherein the medicament is administered to the patient by inhalation, preferably from a DPI. Said disease or condition may be selected from the group of:

treatment of edema, preferably pulmonary edema; and vascular complications in diabetes patients such as micro- and macroangiopathy, myocardial infarction, microvascular cardiac hyperpermeability, stroke, neuropathy, retinopathy, nephropathy or diabetic foot disease; and prevention of edema due to reduction in hyperpermeability, caused by injury of endothelial and/or epithelial layers, preferably edema occurring during treatment of pneumonia, acute lung injury, ARDS, bacterial or viral lung disease, more preferably edema occurring during infection by *Listeria monocytogenes, Streptococcus pneumoniae*, SARS virus, RSV or Influenza virus; and the pulmonary form of altitude sickness.

influenza, if the medicament is administered together with an inhibitor of viral neuraminidase, preferably zanamivir or oseltamivir. A peptide of the invention is already known for use in treatment or prevention for all of the above from EP 1 264 599 B1, EP 2 403 519 A1, WO 2014/001177 A1, and EP 2 640 410 A1.

In said embodiment, in each administration of the dry-powder formulation according to the present invention, the required efficient amount (or dose) comprising the active agent(s) is administered to the individual in need of the administration. Therein, "efficient amount" is the amount sufficiently efficient to cause the intended therapeutic or prophylactic effect, for instance to subdue a further worsening of the disease or condition, treat such worsening or foster curing or cure the disease or condition. Usually, the efficient amount is formulated for an average patient. However, the actually efficient amounts (or doses) may be formulated as to depend on one or more selected from group comprising: particular mode of administration; age, body weight, general health of the patient; severity and progression of the disease or condition.

In another embodiment, the medicament of the present invention is for use in treatment or prevention of influenza, wherein the medicament is administered together with an inhibitor of viral neuraminidase, preferably zanamivir or oseltamivir. The administration may preferably be by a single dry-powder formulation according to the present invention additionally including the inhibitor, or by separately administering the inhibitor.

In the latter embodiment, the inhibitor can be administered to said patient via a mode selected from the group consisting of oral, parenteral, intranasal, inhalation, rectal and topical administration. Examples of suitable neuraminidase inhibitors are listed in WO 2012/065201 A1. According to the invention, neuraminidase inhibitors are comprised in all efficient chemical forms, such as salts, racemic, enantiomerically pure and salt-less forms, as well as enantiomers and diastereomers of the inhibitor. Zanamivir or oseltamivir are preferred because they were particularly successfully used in the treatment of human patients.

In another embodiment, the medicament of the present invention further comprises an inhibitor of viral neuraminidase (i.e. the medicament is a combination formulation), preferably zanamivir or oseltamivir, especially for use in treatment or prevention of influenza, wherein the medicament is administered to a patient by inhalation, preferably from a dry-powder inhaler. Such a combination formulation may simplify administration to the patient. Zanamivir is already approved as a dry-powder medicament (for instance by the US-FDA), for use with the DPI DISKHALER®. Therefore, zanamivir may be especially attractive for combination formulation. In addition, a dry-powder formulation of oseltamivir was found suitable for pulmonary administration (Tang et al., 2013, PMID 24299495, abstract).

According to another aspect, the present invention provides a method for manufacturing the medicament according to the present invention.

The method according to the present invention comprises:
   dissolving or diluting the active agent in a liquid, yielding a solution wherein the carbohydrate content of total solids in solution is less than 5% (w/w), preferably less than 1% (w/w), more preferably less than 0.1% (w/w), especially less than 0.01% (w/w), or, in a most preferred embodiment, said carbohydrate content is 0%.
   removing the solvent from said solution by spray drying, spray-freeze-drying, super-critical fluid precipitation, air-jet milling, lyophilisation or rotary evaporation, preferably by spray drying.

Example 1 shows a particularly preferred embodiment of the method according to the present invention. FIGS. 1 and 2 show material properties of product manufactured by said embodiment.

The the carbohydrate content in the method according to the present invention may be formed by sugar(s) or sugar alcohol(s) such as lactose, maltose, sucrose, trehalose, glucose, sorbitol, maltitol, mannitol and xylitol.

In a preferred embodiment, in the method of the present invention the total solids concentration before removal of the solvent is between 1-10% (w/v), preferably between 2-4% (w/v). In a particularly preferred embodiment of the method of the present invention (see also Example 1), the solvent is removed by spray drying and the inlet temperature of the spray dryer is between 50-110° C., preferably 70-90° C., more preferably 75-85° C. and the outlet temperature of the spray dryer is between 20-80° C., preferably 40-60° C., more preferably 45-55° C.

Definitions

As used herein, a peptide according to the present invention having "no TNF-receptor-binding activity" or "not exhibiting TNF-receptor-binding activity" shall mean: said peptide having/exhibiting no TNF-receptor-binding activity that is sufficient to cause TNF-specific inflammatory activity detrimental to the successful treatment of a patient.

In particular, "TNF-specific inflammatory activity detrimental to the successful treatment of a patient" may mean the following: In an ex vivo safety pharmacological study of said peptide in a human whole blood sample—performed to assess whether addition of said peptide results in the release of the pro-inflammatory marker interleukin-6 (IL-6) from fresh human whole blood—addition of said peptide up to a concentration of 10 mg/ml to said blood sample results in less than 0.5 pg/ml released IL-6 (cf. EP 2 582 385 A1, example 2).

The terms "carrier" and "excipient" are used interchangeably herein. Suitable carriers or excipients are known to the person skilled in the art. Such excipients may comprise substances that enhance isotonicity and chemical stability, buffers and preservatives. Other suitable carriers include any carrier that does not itself induce the production of antibodies in the patient that are harmful for the patient. Examples are well-tolerable proteins, polysaccharides, polylactic acids, polyglycolic acid, polymeric amino acids and amino acid copolymers. Examples of carriers used in spray drying are carbohydrates, in particular sugars or sugar alcohols such as lactose, maltose, sucrose, trehalose, glucose, sorbitol, maltitol, mannitol and xylitol, and polysaccharides such as chitosan. Also used as carriers can be various polymers such as polyethlene glycol (PEG), polyvinylpyrrolidone (PVP), poly(lactic acid) (PLA) and poly(lactic-co-glycolic acid) (PLGA).

Carbohydrates according to the present invention include, without being limited to, saccharides (e.g. monosaccharides such as glucose, fructose and galactose, disaccharides such as sucrose, lactose, trehalose and maltose, polysaccharides such as cellulose or its derivates) and sugar alcohols such as mannitol or sorbitol.

The expressions "does not contain any excipient", "not comprising any excipient" and "having/comprising/containing no excipient" shall not exclude the presence of any excipient in trace amounts, such as less than 10 parts per million. Furthermore, it is evident that the presence of residual moisture in the dry-powder medicament of the present invention is not excluded by the foregoing expressions. The presence of a detectable low level of residual moisture is a consequence of the chemical properties of the peptides contained in the medicament, for some water molecules can remain bound to or coordinated with the peptides upon drying. Preferably, the residual moisture of the inventive dry-powder medicament does not exceed 10% (w/w), in particular it does not exceed 5% (w/w).

The invention is further described in the following examples and the figures, yet without being restricted thereto.

FIG. 1: Peptide A2301 can be successfully spray-dried even without excipients—volume size distributions. A spray-dried powder of peptide AP301 with no excipients (A) has a very similar particle size distribution when compared to a spray-dried powder of AP301/sucrose (4:1 w/w) (B) and AP301/mannitol (4:1 w/w) (C). All three particle size distributions are suitable for a medicament to be administered by means of a dry-powder inhaler.

FIG. 2: Peptide A2301 can be successfully spray-dried even without excipients—scanning electron micrographs. Scanning electron micrographs of spray-dried powders of (A) peptide AP301 with no excipients (B) AP301/sucrose (4:1 w/w) and (C) AP301/mannitol (4:1 w/w). Particle properties are similar, and all dry powders suitable for a medicament to be administered by means of a dry-powder inhaler.

FIG. 3: Sugar(-alcohol) excipients present in typical concentrations inhibit the biological activity of peptide A2301. Shown is the effect of spray-dried and control peptide AP301 on amiloride-sensitive sodium current in A549 cells, as signified by mean values of inward currents during control phase, following addition of AP301 (up to 200 nM from peptide weight) and final addition of amiloride (up to 100 µM) to the bath solution. (A) Peptide control, n=5 (B) "Unformulated" (i.e. formulated not containing excipients) AP301, n=11 (C) AP301 formulated with 20% (w/w) sucrose, n=9 (D) AP301 formulated with 20% (w/w) mannitol, n=9. Cells were patched in whole-cell mode; inward current was elicited at −100 mV. The current is reduced to about 30% in the presence of sucrose or mannitol. Ratio AP301/sugar (alcohol) was 4:1 (w/w). ***: $p<0.0001$ compared with indicated experiment as determined by t test. (NS): non-significant.

Figure 4A:
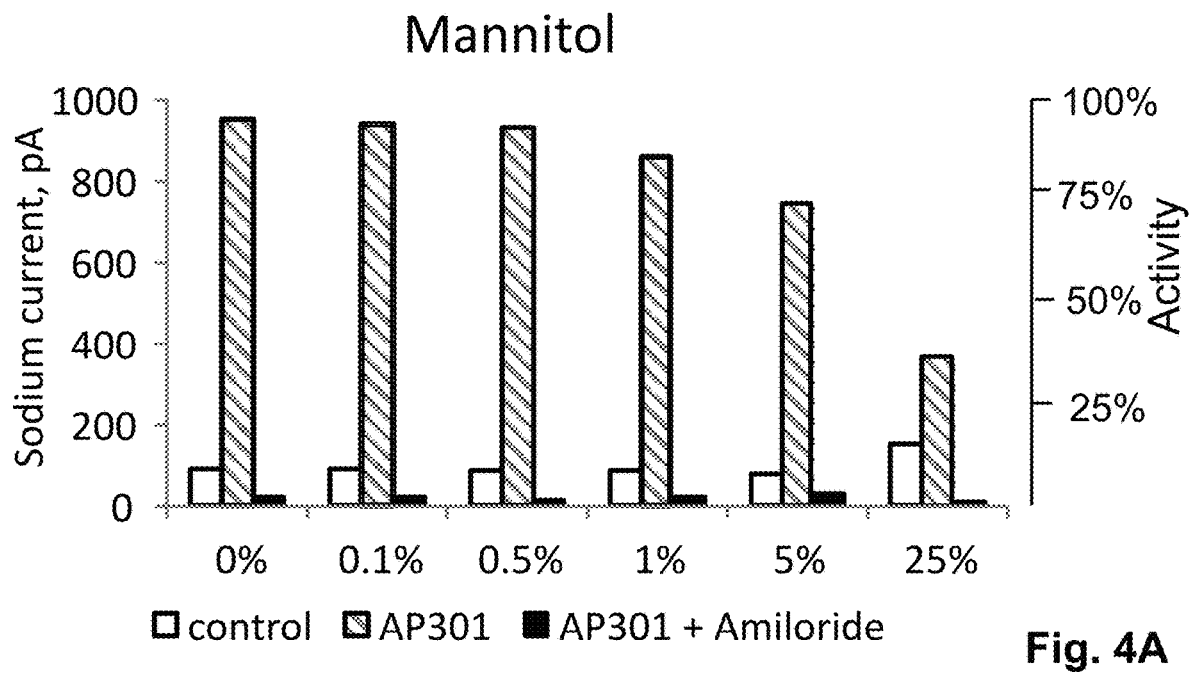
Figure 4B:
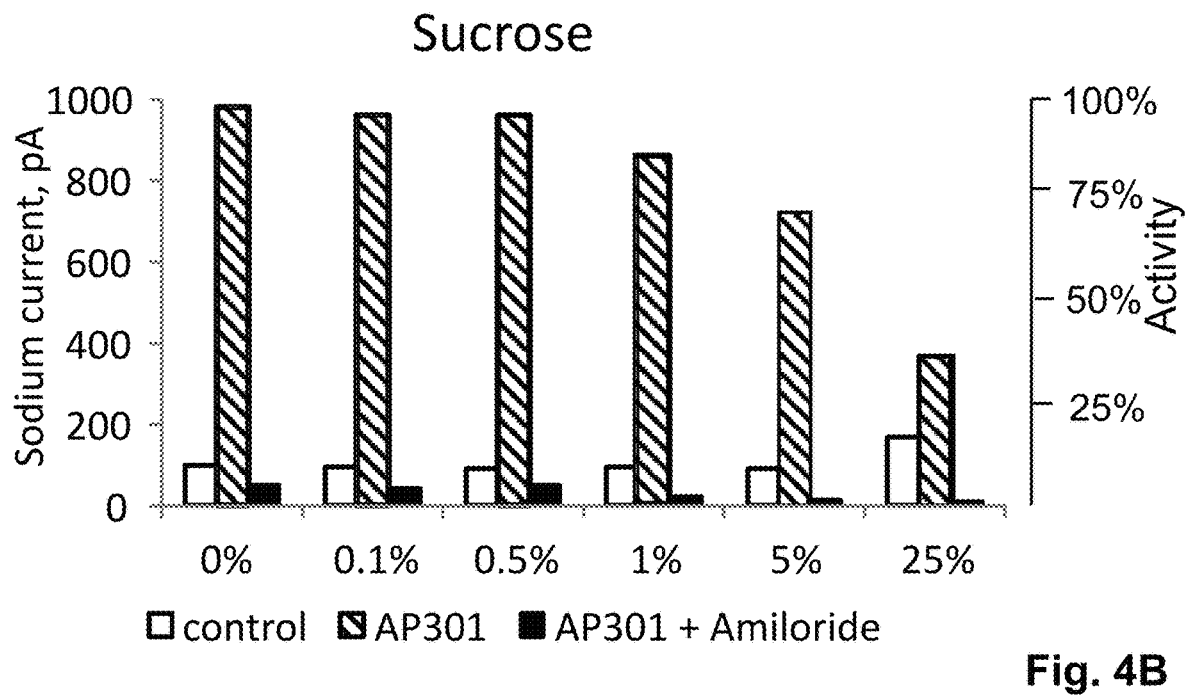

FIG. 4: Inhibitory effect of sugar(-alcohol) on the biological activity of peptide AP301 in an ascending-dose study. Shown is the effect of spray-dried AP301 formulated with increasing concentrations (% w/w) of mannitol (FIG. 4A) or sucrose (FIG. 4B) on amiloride-sensitive sodium current in A549 cells. Control (white bars): Mean values of inward currents during control phase. AP301 (hatched bars): Mean values of inward currents following addition of spray-dried AP301 formulated with X % (w/w) mannitol/sucrose (up to 200 nM from peptide weight). AP301+ Amiloride (black bars): Mean values of inward currents following final addition of amiloride (up to 100 µM) to the bath solution. Cells were patched in whole-cell mode; inward current was elicited at −100 mV.

EXAMPLES

Example 1

Producing Dry Powders of AP301 Formulations

Example 1 discloses a preferred method of manufacturing a medicament according to the present invention. Briefly, a spray-drying device is used to produce said medicament with material properties suitable for administration for DPIs (most importantly, volume size distribution of the particles suitable for DPIs).

The aim of this study was to investigate spray drying as a process for producing a dry powder formulation of synthetic peptide AP301.
Materials and Methods
Spray-Drying AP301 without Excipients (Sample #1)

The frozen AP301 powder was allowed to warm to room temperature for 30 minutes before opening. 1.0 g AP301 powder (containing 862 mg peptide) was added to 33 ml deionised water, to give a total solids concentration of 3% w/v. This was placed on a roller mixer until fully dissolved (~15 minutes).

The solution was spray dried using a Buchi B290 spray dryer, fitted with a high-efficiency cyclone and a Buchi two-fluid nozzle.

The spray dryer was equilibrated by spraying deionised water at 2 ml/min until a steady outlet temperature of 50° C. was maintained. The feed was then switched to the AP301 solution.

After spray drying, the machine was turned off and product was recovered immediately into a glass vial. Most of the product was recovered from the collection jar (~80%), with the remainder recovered from the cyclone.

The vial was placed unsealed in a vacuum oven at ambient temperature (~20° C.) under a vacuum of 800 mbar for 18 hours. The vial was sealed and stored refrigerated.

TABLE 1

| Spray drying conditions | |
| --- | --- |
| Aspirator | 100% |
| Liquid Feed Rate | 2 ml/minute |
| Atomisation Pressure | 6 bar |
| Inlet temperature | 80° C. |
| Outlet temperature | 50° C. |

Spray-Drying AP301 with 20% Sucrose (w/w) (Sample #2)

800 mg AP301 powder (containing 690 mg peptide) was added to 32.4 ml deionised water and placed on a roller mixer until fully dissolved. 172 mg sucrose was added to the solution to give a total solids concentration of 3% w/v, and a peptide to sucrose ratio of 4:1 w/w in the final product.

The solution was spray dried and vacuum dried as described above.
Spray-Drying AP301 with 20% Mannitol (w/w) (Sample #3)

800 mg AP301 powder (containing 690 mg peptide) was added to 32.4 ml deionised water and placed on a roller mixer until fully dissolved. 172 mg mannitol was added to the solution to give a total solids concentration of 3% w/v, and a peptide to mannitol ratio of 4:1 w/w in the final product.

The solution was spray dried and vacuum dried as described above.

TABLE 2

| Summary of AP301 solutions spray dried | | | | |
| --- | --- | --- | --- | --- |
| Sample # | Weight of AP301 powder | Weight of peptide* | Weight of sugar added | Volume of deionised water |
| 1 | 1.0 g | 862 mg | 0 | 33.0 ml |
| 2 | 800 mg | 690 mg | 172 mg sucrose | 32.4 ml |
| 3 | 800 mg | 690 mg | 172 mg mannitol | 32.4 ml |

*AP301 peptide was supplied as a powder in which 1.16 g powder contains 1.0 g peptide The aim of this study was to investigate spray drying as a process for producing a dry powder formulation of synthetic peptide AP301.
Particle Size Analysis Particle size analysis was performed using a SympaTec HELOS particle size analyser with a RODOS disperser. Approximately 50 mg microparticles were placed on the vibrating feeder and fed into the hopper. Dispersal was achieved using compressed air at a pressure of 2 bar.
Scanning Electron Microscopy The surface morphology of the spray-dried particles was studied using a JEOL 6060LV variable pressure scanning electron microscope.
Results AP301 was spray dried both "unformulated" (i.e. formulated without excipients), and with addition of sucrose and mannitol. Particles in the target range of 2-4 µm (FIG. 1) were readily achieved by spray drying the peptide formulations using a Buchi B290 spray dryer, at high atomisation pressure (6 bar) and low liquid feed rate (2 ml/min). These particles were observed, by scanning electron microscopy, to have predominantly collapsed spherical morphology (FIG. 2).

All three feed solutions were successfully spray dried, resulting in fine white powders. Recoveries (yields) were high; in the range 68-78%. The spray dried powders had good handling properties, and could be easily recovered from the collection vessel with minimal static charge.

TABLE 3

Particle size analysis (summary)

| Sample | $X_{10}$* (µm) | $X_{50}$** (µm) | $X_{90}$*** (µm) | VMD**** (µm) |
|---|---|---|---|---|
| #1 | 0.98 | 2.52 | 5.79 | 3.06 |
| #2 | 1.25 | 2.49 | 4.87 | 2.86 |
| #3 | 0.98 | 2.43 | 5.05 | 2.81 |

*10% of microparticles, by volume, below this figure
**50% of microparticles, by volume, below this figure
***90% of microparticles, by volume, below this figure
****Volume mean diameter (The volume mean diameter is also called "mean diameter" herein.)

SEM showed the particles to have predominantly collapsed spherical morphology in all three samples (FIG. 2). This morphology is generally advantageous for pulmonary drug delivery, as hollow low-density particles have lowered aerodynamic diameter and hence improved delivery efficiency. The dimpled surface of the particles may also assist in dispersibility of the powder by minimizing contact areas.

All three samples produced in this study spray dried well to give high yields of powder, within the target particle size range and with promising morphology for pulmonary delivery.

Example 2

In-Vitro Activity Assay of AP301 Dry-Powder Formulations

Example 2 teaches how to test the biological activity of a medicament according to the present invention in an in-vitro assay.

Materials and Methods

Whole-Cell Patch-Clamp

Whole-cell currents were acquired from A549 cells at room temperature (19° C.) 48 hours after plating using an Axopatch 200B amplifier and DigiData 1440A with pCLAMP10.2 software (Axon Instruments, Union City, Calif.). Currents were recorded at 10 kHz and filtered at 5 kHz. Glass coverslips with cultured cells were transferred to a chamber of 1-ml capacity, mounted on the stage of an inverted microscope (Axiovert 100; Carl Zeiss, Oberkochen, Germany). The chamber contained 1 ml bath solution of the following composition (in mM): 145 NaCl, 2.7 KCl, 1.8 CaCl2, 2 MgCl2, 5.5 glucose, and 10 HEPES, adjusted to pH 7.4 with 1 M NaOH solution. The borosilicate glass patch pipettes (Harvard Apparatus, Holliston, Mass.) with resistances of 2 MV were pulled and polished using a DMZ Universal Puller (Zeitz Instruments, Martinsried, Germany). The pipette solution contained the following (in mM): 135 potassium methane sulphonate, 10 KCl, 6 NaCl, 1 Mg2ATP, 2 Na3ATP, 10 HEPES, and 0.5 EGTA, adjusted to pH 7.2 with 1 M KOH solution. After GV-seal formation, the equilibration period of 5 minutes was followed by recordings at holding potentials (Eh) at 0 mV. Gigaseals were continuously monitored during the experiments to avoid an inadequate voltage clamp. For each AP301 formulation of interest, said formulation was added into a bathing solution, up to 200 nM from peptide weight.

Amiloride was added in control experiments to identify the amiloride-sensitive Na-ion current from the total current. The wash-in phase lasted approximately 1 minute. After steady state effects with each indicated compound had been reached, the same clamp protocol was applied as during control recordings. At the end of the experiments with AP301, amiloride was added to show whether the peptide-induced increase in current was due to the amiloride-sensitive Na-ion current. In the washout phase, the control solution was applied onto the patched cells after reaching the steady state wash-in phase. The amiloride-sensitive current was determined by subtracting the whole-cell current measured in the presence of amiloride from that measured in the absence of amiloride at given concentration.

Taken together, the effect of spray-dried and control peptide AP301 on amiloride-sensitive sodium current in A549 cells was measured, as signified by mean values of inward currents during control phase, following addition of AP301 (up to 200 nM from peptide weight) and final addition of amiloride (up to 100 μM) to the bath solution. Cells were patched in whole-cell mode; inward current was elicited at −100 mV.

Results

Sugar(-alcohol) excipients present in a concentration typical for a dry-powder peptide formulation, 20% w/w in this Example (which is lower than the 40% w/w of Exubera, as stated above), markedly reduce the biological activity of a dry-powder formulation containing peptide AP301 (FIG. 3). The current as an indicator of biological activity is reduced to about 30% of the normally induced level in the presence of 20% (w/w) sucrose or 20% (w/w) mannitol.

Example 3

In-Vitro Activity Assay of AP301 Dry-Powder Formulations in an Ascending-Carbohydrate-Dose Study Dry-powder formulations of AP301 with 0%, 0.1%, 0.5%, 1%, 5% and 25% (w/w) mannitol (FIG. 4A) or sucrose (FIG. 4B) were tested for their in-vitro activity in a whole-cell patch-clamp assay. The assay setup was similar to what was described in Materials and Methods of Example 2.

Results

As anticipated by Example 2, sucrose and mannitol have a dose-dependent inhibitory effect on the biological activity of peptide AP301. The inhibitory effect becomes markedly detrimental at a sucrose/mannitol concentration of 1% (w/w) (activity reduction by about 10%) and especially detrimental at a sucrose/mannitol concentration of 5% (w/w) (activity reduction by about 30%).

The invention claimed is:

1. A method for manufacturing a dry-powder medicament, comprising the steps of:
   providing a cyclized peptide as an active agent, wherein the peptide consists of 7-17 amino acids and comprises the hexamer TPEGAE (SEQ ID NO: 2), wherein the peptide is cyclic, and wherein the peptide does not exhibit TNF-receptor-binding activity;
   dissolving or diluting the active agent, optionally together with a carbohydrate, in a solvent, wherein the solvent consists of water, thereby yielding a solution with a carbohydrate content of total solids in solution of less than 5% (w/w); and
   removing the solvent from said solution by spray drying, spray-freeze-drying, supercritical fluid precipitation, air-jet milling, lyophilisation or rotary evaporation to obtain the dry-powder medicament.

2. The method according to claim 1, wherein the solution has a sugar content of total solids in solution of less than 5% and a sugar alcohol content of total solids in solution of less than 5% (w/w).

3. The method according to claim 1, wherein the solvent is removed by spray drying and the inlet temperature of the spray dryer is between 50-110° C. and the outlet temperature of the spray dryer is between 20-80° C.

4. The method according to claim 1, wherein the carbohydrate content of total solids in solution is less than 1% (w/w).

5. The method according to claim 1, wherein the carbohydrate content of total solids in solution is less than 0.1% (w/w).

6. The method according to claim 1, wherein the carbohydrate content of total solids in solution is less than 0.01% (w/w).

7. The method according to claim 1, wherein the total solids concentration before removal of the solvent is between 2-4% (w/v).

8. The method according to claim 3, wherein the solvent is removed by spray drying and the inlet temperature of the spray dryer is between 70-90° C.

9. The method according to claim 3, wherein the solvent is removed by spray drying and the inlet temperature of the spray dryer is between 75-85° C.

10. The method according to claim 3, wherein the solvent is removed by spray drying and the outlet temperature of the spray dryer is between 40-60° C.

11. The method according to claim 3, wherein the solvent is removed by spray drying and the outlet temperature of the spray dryer is between 45-55° C.

12. The method according to claim 1, wherein the total solids concentration before removal of the solvent is between 1-10% (w/v).

13. The method according to claim 1, wherein the medicament does not contain any excipient.

14. The method according to claim 1, wherein the medicament consists essentially of the peptide.

15. The method according to claim 14, wherein the peptide comprises the amino acid sequence CGQRETPEGAEAKPWYC (SEQ ID NO: 1).

16. The method according to claim 1, wherein the peptide comprises the amino acid sequence CGQRETPEGAEAKPWYC (SEQ ID NO: 1).

17. The method according to claim 1, wherein the medicament consists of powder particles of a mean diameter of 0.5 to 10 micrometers.

18. The method according to claim 17, wherein the medicament consists of powder particles of a mean diameter of 1 to 5 micrometers.

19. The method according to claim 18, wherein the medicament consists of powder particles of a mean diameter of 1 to 3.5 micrometers.

20. A method for manufacturing a dry-powder medicament, comprising the steps of:
   providing a cyclized peptide as an active agent, wherein the peptide consists of 7-17 amino acids and comprises the hexamer TPEGAE (SEP ID NO: 2\ wherein the peptide is cyclic, and wherein the peptide does not exhibit TNF-receptor-binding activity;
   dissolving or diluting the active agent in a solvent, thereby yielding a solution with the total solids in solution consisting of the peptide; and
   removing the solvent from said solution by spray drying, spray-freeze-drying, supercritical fluid precipitation, air-jet milling, lyophilisation or rotary evaporation to obtain the dry-powder medicament.

* * * * *

SEQUENCE LISTING

```
<160> NUMBER OF SEQ ID NOS: 6

<210> SEQ ID NO 1
<211> LENGTH: 17
```

```
<212> TYPE: PRT
<213> ORGANISM: Artificial Sequence
<220> FEATURE:
<223> OTHER INFORMATION: AP301 peptide

<400> SEQUENCE: 1

Cys Gly Gln Arg Glu Thr Pro Glu Gly Ala Glu Ala Lys Pro Trp Tyr
1               5                   10                  15

Cys

<210> SEQ ID NO 2
<211> LENGTH: 6
<212> TYPE: PRT
<213> ORGANISM: Artificial Sequence
<220> FEATURE:
<223> OTHER INFORMATION: peptide sequence

<400> SEQUENCE: 2

Thr Pro Glu Gly Ala Glu
1               5

<210> SEQ ID NO 3
<211> LENGTH: 14
<212> TYPE: PRT
<213> ORGANISM: Artificial Sequence
<220> FEATURE:
<223> OTHER INFORMATION: peptide

<400> SEQUENCE: 3

Gln Arg Glu Thr Pro Glu Gly Ala Glu Ala Lys Pro Trp Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: peptide

<400> SEQUENCE: 4

Pro Lys Asp Thr Pro Glu Gly Ala Glu Leu Lys Pro Trp Tyr
1               5                   10

<210> SEQ ID NO 5
<211> LENGTH: 17
<212> TYPE: PRT
<213> ORGANISM: Artificial Sequence
<220> FEATURE:
<223> OTHER INFORMATION: peptide

<400> SEQUENCE: 5

Cys Gly Pro Lys Asp Thr Pro Glu Gly Ala Glu Leu Lys Pro Trp Tyr
1               5                   10                  15

Cys

<210> SEQ ID NO 6
<211> LENGTH: 6
<212> TYPE: PRT
<213> ORGANISM: Artificial Sequence
<220> FEATURE:
<223> OTHER INFORMATION: peptide sequence
<220> FEATURE:
<221> NAME/KEY: VARIANT
```

```
<222> LOCATION: 2,4,5
<223> OTHER INFORMATION: any natural or non-natural amino-acid

<400> SEQUENCE: 6

Thr Xaa Glu Xaa Xaa Glu
1               5
```